United States Patent
Tsuji et al.

[11] Patent Number: 5,900,129
[45] Date of Patent: May 4, 1999

[54] OXYGEN CONCENTRATION SENSOR

[75] Inventors: Nobuyuki Tsuji, Nukata-gun; Takashi Kojima, Kasugai; Isao Watanabe, Nagoya; Masahiro Hamaya, Anjo; Minoru Ohta, Okazaki; Naoto Miwa, Tsushima, all of Japan

[73] Assignee: Nippondenso Co., Ltd., Kariya, Japan

[21] Appl. No.: 08/659,642

[22] Filed: Jun. 6, 1996

[30] Foreign Application Priority Data

Jun. 7, 1995 [JP] Japan ................................ 7-166983
Feb. 23, 1996 [JP] Japan ................................ 8-062166

[51] Int. Cl.$^6$ .................................................. G01N 27/26
[52] U.S. Cl. .......................... 204/427; 204/424; 204/428; 205/784
[58] Field of Search ............................... 422/94; 204/424, 204/410, 426, 427

[56] References Cited

U.S. PATENT DOCUMENTS

| | | | |
|---|---|---|---|
| 4,123,131 | 10/1978 | Pearce, Jr. et al. | 439/206 |
| 4,187,163 | 2/1980 | Steinke et al. | 204/428 |
| 4,556,475 | 12/1985 | Bayha et al. | 204/427 |
| 4,786,399 | 11/1988 | Wertheimer et al. | 435/5 |
| 4,948,491 | 8/1990 | Kato et al. | 204/424 |
| 5,049,255 | 9/1991 | Wolf et al. | 204/428 |

FOREIGN PATENT DOCUMENTS

| | | |
|---|---|---|
| 0056585 | 7/1982 | European Pat. Off. . |
| 0087626 | 9/1983 | European Pat. Off. . |
| 0132691 | 2/1985 | European Pat. Off. . |
| 0702229 | 9/1994 | European Pat. Off. . |
| 2702578 | 7/1978 | Germany . |
| 2-060864 | 5/1990 | Japan . |
| 6-010306 | 3/1994 | Japan . |
| 6-031421 | 8/1994 | Japan . |

*Primary Examiner*—Ponnathapura Achutamurthy
*Assistant Examiner*—P. Ponnaluri
*Attorney, Agent, or Firm*—Pillsbury Madison & Sutro LLP

[57] ABSTRACT

An oxygen concentration sensor having excellent sealing performance between a lead wire and a lead wire insertion hole includes a sensor element disposed insertedly into a housing, protective covers disposed at an end portion of the housing, lead wires inserted into the protective covers, and an elastic insulating member disposed inside the protective covers and having a lead wire insertion hole for inserting the lead wires. The lead wire insertion hole in the elastic insulating member has a rib protruding in the radial direction. The elastic insulating member is caulked and fixed by the protective covers.

25 Claims, 8 Drawing Sheets

OXYGEN CONCENTRATION SENSOR

CROSS-REFERENCE TO RELATED APPLICATIONS

The present application is related to and claims priority from Japanese Patent Application Nos. Hei 7-166983 and Hei 8-62166, incorporated herein by reference.

BACKGROUND OF THE INVENTION

1. Field of the Invention

The present invention relates to an oxygen concentration sensor employed for air/fuel ratio control or the like of an automobile engine.

2. Description of Related Art

An oxygen concentration sensor as described below has been conventionally installed in an exhaust pipe or the like composing part of the exhaust system of an automobile engine to control an air/fuel ratio of the automobile engine.

An oxygen concentration sensor generally includes a sensor element inserted into a housing, a protective cover disposed at an end portion of the housing, a lead wire inserted into the protective cover, and an elastic insulating member disposed inside the protective cover and also having a lead wire insertion hole for receiving the lead wire. The lead wire inserted into the lead wire insertion hole is sealed and fixed into the above-described lead wire insertion hole by caulking it to the protective cover in the radial direction (see, e.g., Japanese Utility Model Laid-Open No. Hei 2-60864).

Recently, however, the fixing position of the above-described oxygen concentration sensor has been varied. For instance, it has been frequently installed at the downstream side of the exhaust pipe. In this case, the oxygen concentration sensor is splashed with water thrown out by a tire or the like during the driving of an vehicle or it may be doused in puddles. If water enters the inside of the oxygen concentration sensor due to dousing or splashing of water, it causes disorders and malfunctions such as deterioration of an output of the oxygen concentration sensor and cracks of the sensor element due to the dousing or splashing of water.

In recent years, moreover, the number of oxygen concentration sensors having a built-in heater in addition to taking out a grounding lead, and laminated oxygen concentration sensors having a two-cell type sensing element including many lead wires has been increasing. Since a large number of the lead wires are disposed inside the protective cover in these oxygen concentration sensors, a larger quantity of lead wire insertion holes have to be disposed in the elastic insulating member.

In the elastic insulating member having the above-described multiple lead wire insertion holes, numerous thin and a thick portions are disposed in close proximity to one another. In such a situation, when a lead wire is inserted into the above-described elastic insulating member and the protective cover is caulked to seal and fix the lead wire on the elastic insulating member, compression stress imposed on the elastic insulating member by caulking the protective cover is concentrated on a thin portion of the elastic insulating member such as an easily deformed portion between the lead wire insertion hole and the outer periphery of the elastic insulating member, so that the compression stress in that portion is increased. On the other hand, the stress in a thick portion such as a central portion of the above-specified elastic insulating member is decreased.

In short, compression stress imposed on each portion in the above-described elastic insulating member may not be even. Accordingly, the oxygen concentration sensor including the elastic insulating member having many lead wire insertion holes has insufficient sealing performance on a contact surface between the lead wires and the lead wire insertion holes. In this case, when the oxygen concentration sensor is splashed with water, the water may easily go into the interior of the oxygen concentration sensor through the above-described lead wire insertion holes.

Furthermore, compression stress imposed on each portion is in an uneven state on the elastic insulating member having many lead wire insertion holes as described above. When such an elastic insulating member is exposed to high ambient temperatures, a large amount of compression stress is imposed on it; thus, a portion thereof is deformed to a great extent and also loses its elasticity and wears out, so that portions in such a state can no longer seal between the lead wire insertion holes and the lead wires.

When an oxygen concentration sensor as described above is employed for controlling an air/fuel ratio in an engine, the exterior temperature of the oxygen concentration sensor comes from radiant heat from the exhaust pipe or the like having high temperature exhaust gas passing therethrough. In the above environment, a problem in which the elastic insulating member looses elasticity in such a high temperature environment is apt to happen more than ever before.

SUMMARY OF THE INVENTION

In light of these problems, the present invention has an object of providing an oxygen concentration sensor having excellent sealing performance between a lead wire and a lead wire insertion hole.

The above object is achieved according to a first aspect of the present invention by providing an oxygen concentration sensor including a sensor element disposed in a housing, a protective cover disposed at an end portion of the housing, a lead wire inserted into the protective cover, and an elastic insulating member disposed inside the protective cover and also having a lead wire insertion hole for inserting the lead wire. The lead wire insertion hole in the above-described elastic insulating member has a rib protruding in the radial direction. In addition, the elastic insulating member is caulked into and fixed by the protective cover. The rib can be easily deformed by press-fitting the lead wire into the above-described lead wire insertion hole, which ensures the stable and certain formation of a seal between the lead wire and the lead wire insertion hole. Thus, even if the oxygen concentration sensor is splashed with water, the water never goes inside the oxygen concentration sensor.

After disposing the elastic insulating member inside the protective cover, the elastic insulating member can be fixed in the protective cover by caulking the protective cover and the elastic insulating member together.

In addition to easily fixing the elastic insulating member inside the protective cover, the rib further deforms at the time of caulking, which further ensures stable and reliable sealing between the lead wire and the lead wire insertion hole.

Moreover, the protective cover can be caulked on the outer periphery of the protective cover from the outside to the inside in the diametrical direction at one portion or plural portions in the range having the elastic insulating member in the axial direction.

The above-described rib is composed of a single or plural protruding portion or portions disposed on the inner wall of the lead wire insertion hole. The protruding portion or portions can be formed in a wide variety of shapes such as arc shapes or triangle shapes.

The above-described lead wire insertion hole or holes are composed of a single through hole or plural through holes passing through from the upper portion of the elastic insulating member to the lower portion in the axial direction thereof.

The elastic insulating member should be preferably made of a rubber material or the like having heat resistance. For example, fluoro rubber is recommended as a rubber material. Depending on the environment in which the oxygen concentration sensor is used, acrylic rubber, silicone rubber or the like can be also employed as the above-described rubber material.

The above-described lead wire is, for instance, an output wire of the sensor element, a grounding wire connected to the sensor element, or an electric power supply wire to a heater in the oxygen concentration sensor. There may be more than one lead wire.

Next, it is preferable that at least the rib on the elastic insulating member is caulked and fixed by the protective cover. Thus, even if the rib does not deform only in the operation of press-fitting the lead wire or wires due to a clearance between the diameter of the lead wire or wires and the lead wire insertion hole or holes, stable and reliable sealing between the lead wire or wires and the lead wire insertion hole or holes can be ensured. Therefore, it is unnecessary to worry about dimensional accuracy of the lead wire or wires and the lead wire insertion hole or holes, thereby ensuring a certain allowance between the lead wire or wires and the lead wire insertion hole or holes in view of dimensional design, so that both of them can be easily installed. Furthermore, they can be manufactured at low cost.

As far as the elastic insulating member is concerned, it should also include an air inlet passing through the inside of the oxygen concentration sensor and a hard water repellent filter insertedly disposed in the air inlet. A large amount of the air as reference gas required to detect oxygen concentration can be efficiently introduced by disposing the air inlet in the elastic insulating member. Accordingly, the air/fuel ratio can be detected with high accuracy even if a situation requires a large amount of reference gas.

The air inlet which has the same shape as the above-described lead wire insertion hole is composed of a through hole passing from the upper portion of the elastic insulating member to the lower portion thereof parallel to its central axis. It is preferable to dispose the air inlet at the center of the elastic insulating member.

The water repellent filter is disposed in the air inlet so that it can prevent water from going inside through the air inlet exposed to the outside. The above-specified hard water repellent filter acts as a rigid core material in the softer elastic insulating member, which can enhance the strength of the elastic insulating member.

As described earlier, since the water repellent filter is hard and acts as a rigid core material, the strength of the soft elastic insulating member can be reinforced. The difference of thickness in each portion on the elastic insulating member can be smaller by disposing the water repellent filter particularly at the center in the diametrical direction of the elastic insulating member. Stress imposed on each portion of the elastic insulating member can be more consistent.

It is also desirable to dispose a protruding rib in a radial direction inside the hole of the air inlet where the water repellent filter is insertedly disposed in the elastic insulating member. Thus, the same excellent sealing performance between the lead wire or wires and the lead wire insertion hole or holes can be provided between the air inlet and the water repellent filter.

Preferably, at least one rib described above is formed in the shape of a continuous ring on the inner wall of the air inlet or the lead wire insertion hole or holes. The height of the continuous ring-shaped rib is preferably 0.05–0.4 mm in an original, uncompressed state before caulking.

Accordingly, sealing between the lead wire or wires and the lead wire insertion hole or holes can be ensured on the entire periphery of the lead wire or wires and the lead wire insertion hole or holes, in addition to the same sealing effect between the water repellent filter and the air inlet on the entire periphery of both.

When the height of the rib is too short, i.e., less than 0.5 mm, sealing performance between the sealing member and the air inlet or lead wire may not be ensured. On the other hand, when the height of the rib exceeds 0.4 mm, it may cause difficulty in molding the elastic insulating member. Also, the rib may hamper the lead wire or wires and the water repellent filter from press-fitting, which reduces efficiency at the time of assembling.

As used herein, the "height of the rib" means the distance between the shortest portion of the inner wall of the air inlet and the lead wire insertion hole and the highest portion of the rib.

Other objects and features of the invention will be appear in the course of the description thereof, which follows.

BRIEF DESCRIPTION OF THE DRAWINGS

Additional objects and advantages of the present invention will be more readily apparent from the following detailed description of preferred embodiments thereof when taken together with the accompanying drawings in which.

DETAILED DESCRIPTION OF THE PRESENTLY PREFERRED EXEMPLARY EMBODIMENTS

The preferred embodiments of the present invention are hereinafter described with reference to the accompanying drawings.

Figure 5:
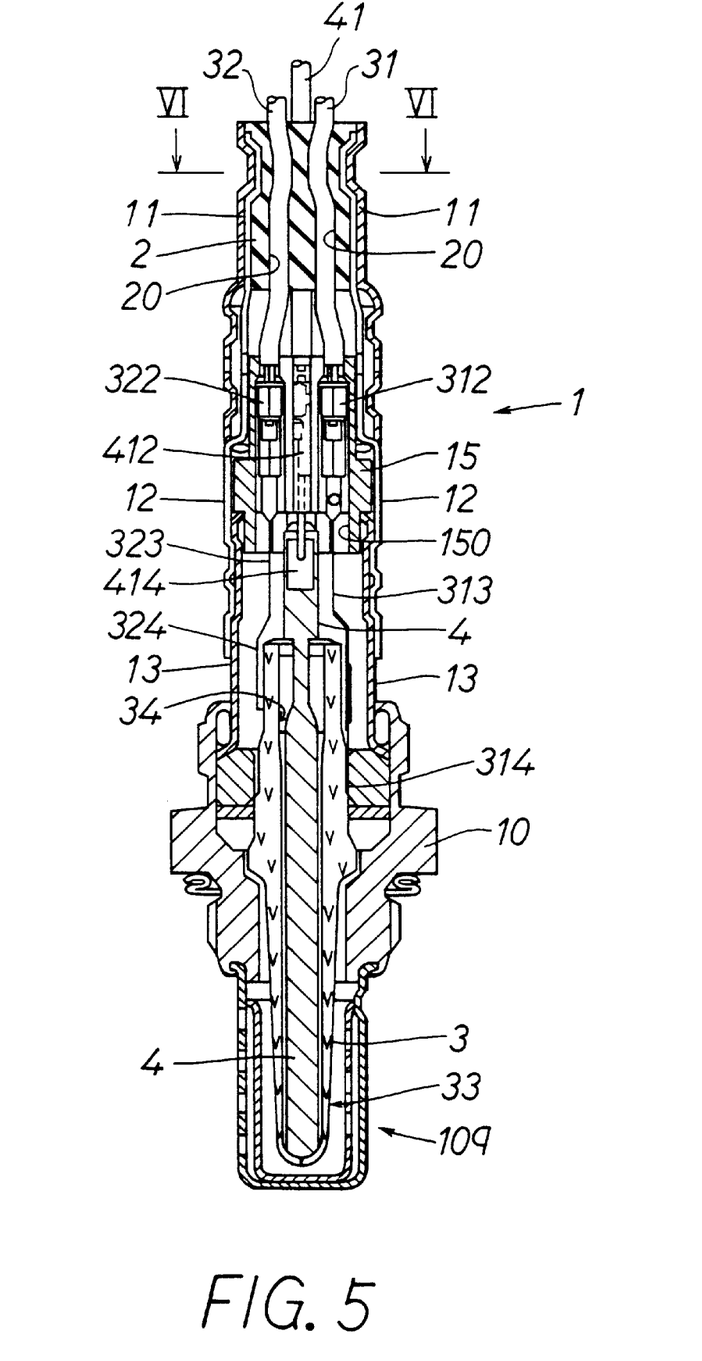
FIG. 5 is a longitudinal cross-sectional view of the oxygen concentration sensor according to the first embodiment.

As shown in FIG. 5, an oxygen concentration sensor 1 according to the first embodiment of the present invention includes a sensor element 3 disposed in a housing 10, protective covers 11 and 12 disposed at an end portion of the housing 10, lead wires 31, 32, 41, and 42 inserted into the protective covers 11 and 12, and an elastic insulating member 2 disposed inside the protective covers 11 and 12 and also having a lead wire insertion hole 20 for receiving the lead wires 31, 32, 41, and 42.

As shown in FIGS. 2A–3B, the lead wire insertion hole 20 in the elastic insulating member 2 has a rib 21 protruding in the radial direction thereof. The elastic insulating member 2 is caulked to and fixed by the protective covers 11 and 12.

Figure 2A:
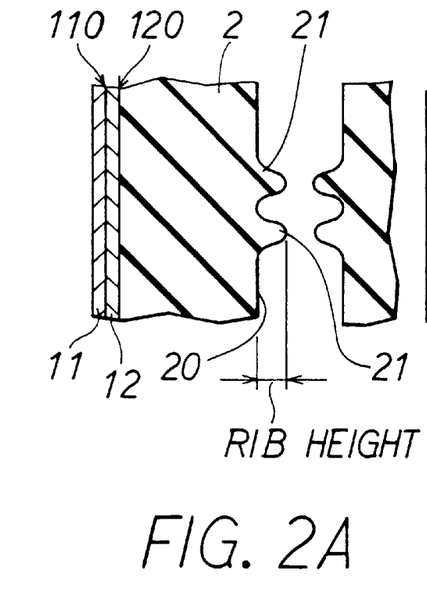
FIG. 2A is a longitudinal cross-sectional view of a sealing member according to the first embodiment before caulking a rib.

Four lead wire insertion holes 20 are disposed in the elastic insulating member 2. Two are holes to receive the lead wires 31 and 32 connected to the sensor element 3. The other two are holes to receive the lead wires 41 and 42 connected to a heater 4 built inside the sensor element 3.

As shown in FIG. 2A, the rib 21 protrudes in an arc shape on the inner wall of the lead wire insertion hole 20 and forms a continuous ring having two steps up and down in the axial direction of the elastic insulating member 2. Furthermore, as shown in FIG. 3A, the above-described shaped rib 21 can be replaced by a rib 219 protruding in the shape of a triangular three-step on the inner wall of the lead wire insertion hole 20.

Figure 3A:
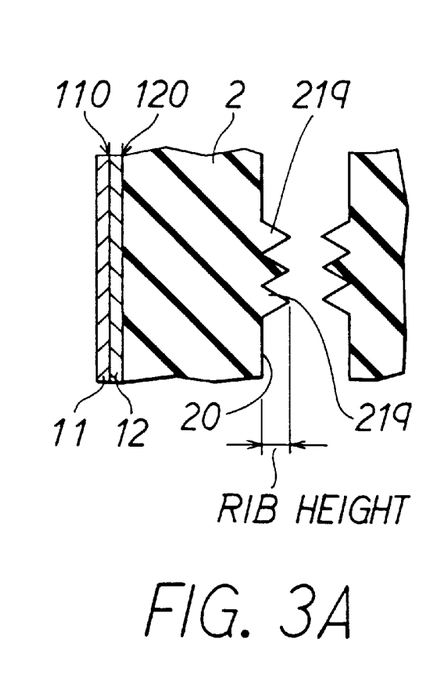
FIG. 3A is a longitudinal cross-sectional view of a sealing member according to a variation on the first embodiment before caulking a rib.

The numerals 110 and 120 in FIG. 2A and FIG. 3A are clearances between the elastic insulating member 2 and the protective covers 11 and 12 before caulking.

As shown in FIG. 5, having a solid electrolyte made of zirconia or the like formed in a cylindrical shape, the sensor element 3 is sealed and fixed to the housing 10. The sensor element 3 has an atmospheric chamber inside and an inner electrode 34 facing the atmospheric chamber.

A measured gas cover 109 is disposed at the bottom of the housing 10 and the cover 109 defines the measured gas chamber. The sensor element 3 has an outer electrode 33 facing the measured gas chamber.

A cover 13 is caulked to and fixed at the upper portion of the housing 10. A protective cover 12 is caulked to and fixed at the upper portion of the cover 13. The protective cover 11 is caulked to and fixed at the upper portion of the protective cover 12.

The sensor element 3 has respective output contacts 314 and 324 enabling external connection of the outer electrode 33 and the inner electrode 34. Output wires 313 and 323 extending from the contacts are connected to respective terminals 312 and 322 through an insertion hole 150 disposed on an insulator 15. The terminals 312 and 322 are connected to the above-described lead wires 31 and 32.

A heater 4 is inserted into the atmospheric chamber of the sensor element 3. An electric terminal 414 for supplying electricity to the heater 4 is connected to a thin wire. The thin wire is connected to the lead wire 41 via a terminal 412 in the insertion hole 150 disposed in the insulator 15. Although it is not shown in FIG. 5, the lead wire 42 also provides an electrical connection to the heater 4 in the same manner as in the lead wire 41.

Figure 1:
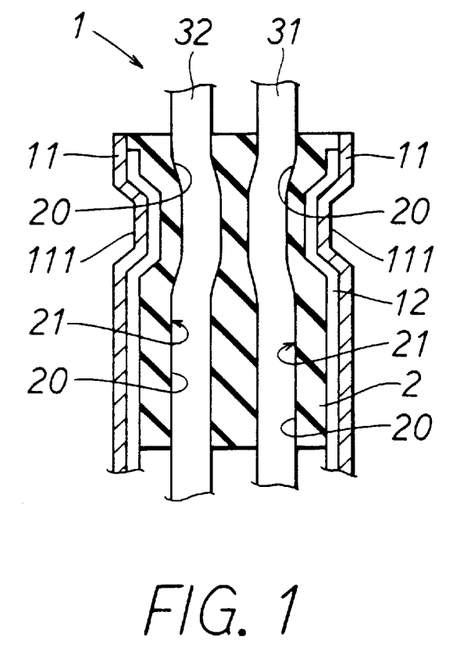
FIG. 1 is a longitudinal cross-sectional view of a portion of an oxygen concentration sensor according to a first preferred embodiment of the present invention.
Figure 4:
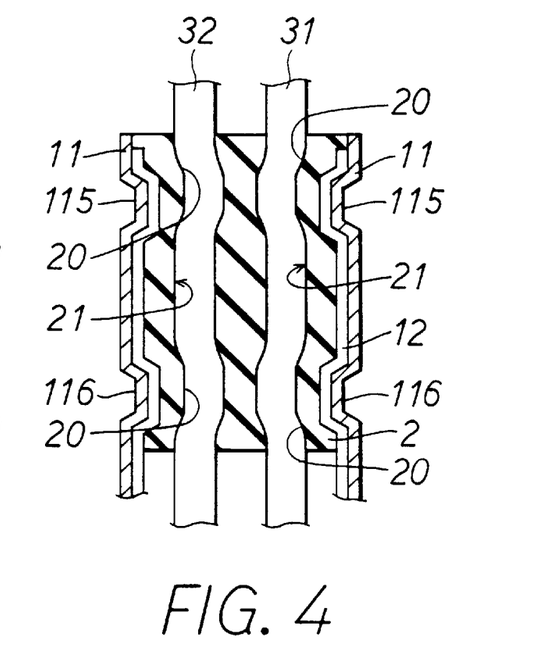
FIG. 4 is a longitudinal cross-sectional view of a main portion of another variation on the oxygen concentration sensor according to the first embodiment.

As shown in FIG. 1, the elastic insulating member 2 is caulked to and fixed to the upper side 111 of the protective covers 11 and 12 and supports the lead wires 31, 32, 41, and 42. As shown in FIG. 4, the lead wires 31, 32, 41, and 42 can be fixed by caulking two portions at the upper portion 115 and the lower portion 116 of the elastic insulating member 2.

The effects and operation according to the above-described embodiment are described below.

Figure 2B:
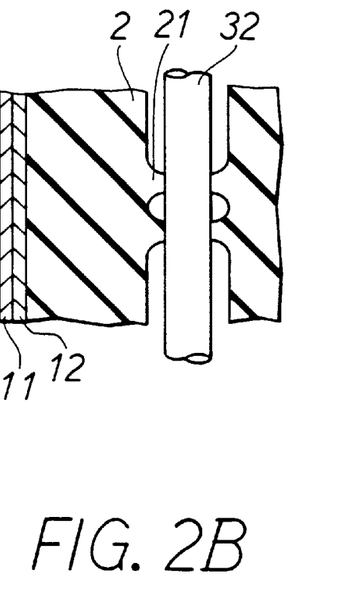
FIG. 2B is a longitudinal cross-sectional view thereof after caulking the rib.
Figure 3B:
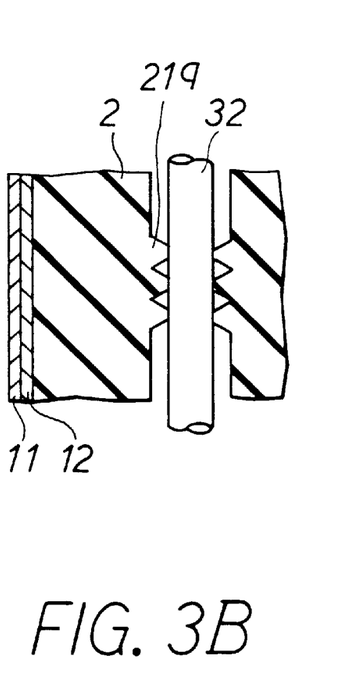
FIG. 3B is a longitudinal cross-sectional view thereof after caulking the rib.

Since the radially protruding rib 2 is disposed on the lead wire insertion hole 20 in the elastic insulating member 2 in the oxygen concentration sensor 1 according to the present embodiment, the rib 21 easily deforms as shown in FIG. 2B and FIG. 3B by press-fitting the lead wires 31, 32, 41, and 42 into the lead wire insertion hole 20.

Thus, the rib can help stably form a seal between the lead wires 31, 32, 41, and 42 and the lead wire insertion hole 20. Even if the oxygen concentration sensor 1 is drenched with water, the water does not go inside the oxygen concentration sensor 1.

As for fixing the elastic insulating member 2 in the protective covers 11 and 12, the elastic insulating member 2 can be caulked with the protective covers 11 and 12 comprehensively after disposing the elastic insulating member 2 inside the protective covers 11 and 12.

Therefore, in addition to easily fixing the elastic insulating member 2 inside the protective covers 11 and 12, the rib 2 further deforms at the time of caulking, which enhances the stability and security of the seal between the lead wires 31, 32, 41, and 42 and the lead wire insertion hole 20.

Moreover, in the present embodiment, the rib 21 is disposed in a ring shape with respect to the lead wire insertion hole 20, which ensures sealing between the lead wires 31, 32, 41, and 42 and the lead wire insertion hole 20 on the entire periphery thereof.

Accordingly, the present embodiment can provide the oxygen concentration sensor 1 having a remarkable sealing performance between the lead wires 31, 32, 41, and 42 and the lead wire insertion hole 20.

Figure 6:
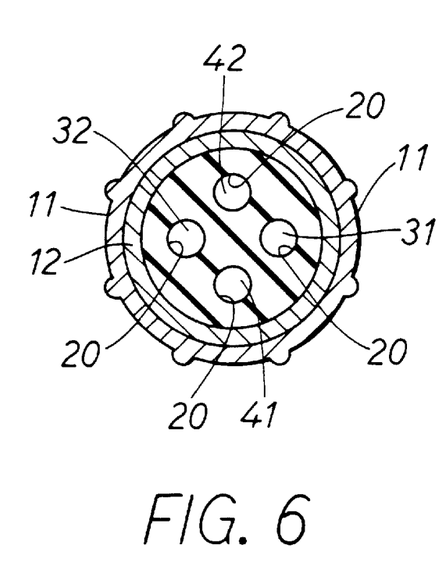
FIG. 6 is a radial cross-sectional view taken along line VI—VI of FIG. 5.
Figure 7:
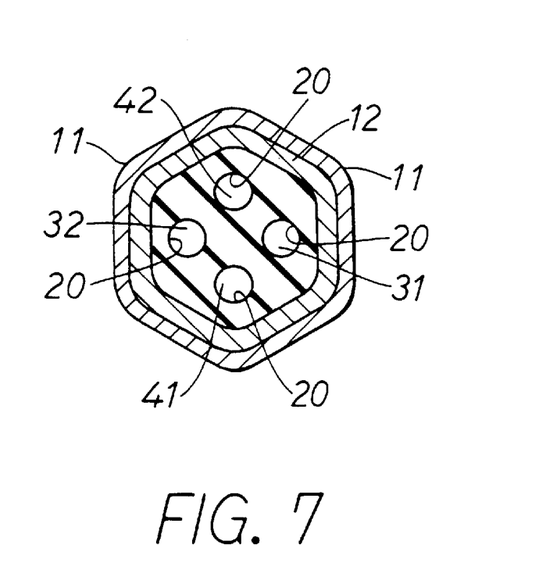
FIG. 7 is a radial cross-sectional view of a main portion of another variation on the oxygen concentration sensor according to the first embodiment.

Although the shape of caulking of the protective covers 11 and 12 in the oxygen concentration sensor 1 according to the present embodiment is preferably circular as shown in FIG. 6, it can be caulked in the shape of a hexagon as shown in FIG. 7.

Figure 8:
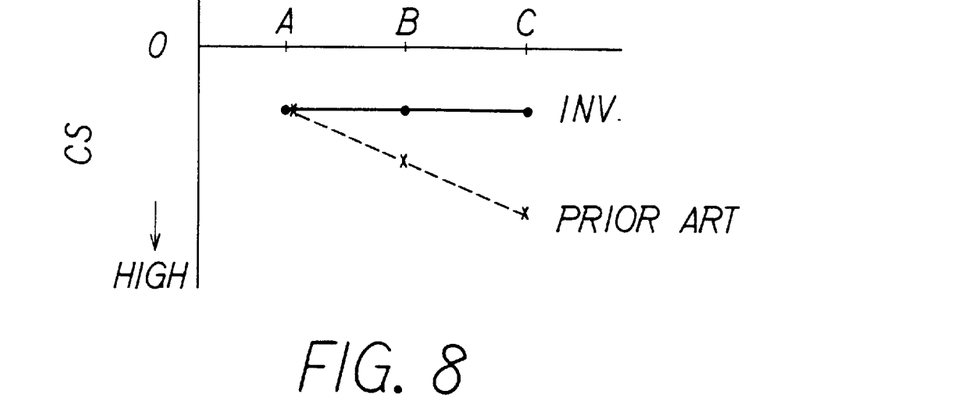
FIG. 8 is a graph showing a compression permanent distortion rate in each portion of an elastic insulating member according to the first embodiment.
Figure 9:
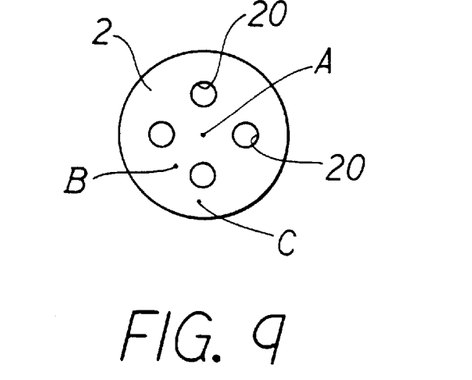
FIG. 9 is an explanatory view of a cross-section of an elastic insulating member used to generate the data shown in FIG. 8.

The compression permanent distortion rate in each portion of an elastic insulating member related to the present invention caulked by a protective cover as shown in FIGS. 8 and 9 will now be explained with reference to a comparative prior art example.

First of all, an elastic insulating member related to the present invention in the shape shown in FIG. 2 of the first embodiment was prepared. Also, as a comparative example, a conventional elastic insulating member which has the same material and shape as in the above-described elastic insulating member was prepared; however, this comparative member does not have a rib. As shown in FIG. 9, respective compression permanent distortion rates were measured and compared at such three points as portions A, B, and C in the above-specified elastic insulating members.

First, in the actual measurement, after installing the above-described elastic insulating member in the oxygen concentration sensor shown in FIG. 5 of the first embodiment, the sensor element of the oxygen concentration sensor was heated to 600°. Second, the above-described oxygen concentration sensor was disassembled and the elastic insulating member removed therefrom.

The method of measuring the above-specified compression permanent distortion is described as follows. First, the thickness of respective portions A, B, and C of the elastic insulating member were measured three times—before assembling, after assembling, and thirty minutes after disassembling. Assuming the distortion before assembling is t0, the distortion after assembling is t2, and the distortion thirty minutes after disassembling at the completion of the test is t1 in the above-described measurement, the above compression permanent distortion rate CS (%) is provided by the following equation (1), and values therefrom are shown in FIG. 8.

$$CS = \{(t0-t1)/(t0-t2)\} \times 100 \quad (1)$$

As shown in the same Figure, the compression permanent distortion rates at portions A, B, and C in the elastic insulating member according to the present invention are substantially equal.

However, in a conventional elastic insulating member, the compression permanent distortion rate of the portion A which is the center of the elastic insulating member was the smallest, and the compression permanent distortion rate at the portion C near the outer periphery of the elastic insulating member was the largest.

Accordingly, the stress imposed on each portion of the elastic insulating member can be made generally equal by disposing a rib in the lead wire insertion hole.

Figure 10:
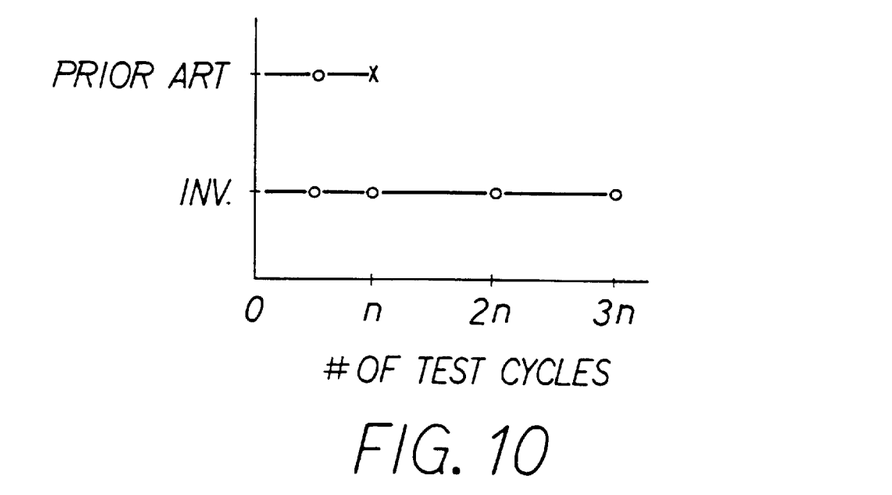
FIG. 10 is a graph showing water resistance in an oxygen concentration sensor in the first embodiment and in a comparative prior art example.

FIG. 10 explains water resistance of oxygen concentration sensors according to the present invention and a conventional device. First, an oxygen concentration sensor according to the embodiment shown in FIG. 5 was prepared. However, the shape of the elastic insulating member is the same as in FIG. 2. Furthermore, the same type of the above-described oxygen concentration sensor which does not have a rib in the lead wire insertion hole in the elastic insulating member was prepared as the comparative example.

In the water resistance test, first, the above two oxygen concentration sensors were installed on devices simulating an exhaust pipe having rich combustion gas flowing therethrough, so that the sensor element has a high temperature (i.e., high enough to enable the sensor element to detect oxygen concentration) and also the temperature of the elastic insulating member has been set to a desired temperature (240° C.) to enable measurement of the sensor output of the oxygen concentration sensors. After a predetermined period passes, the above oxygen concentration sensors were repeatedly sprayed with water until the sensor output became abnormal.

FIG. 10 shows the above measured results. According to this graph, it was found that the oxygen concentration sensor having a rib in the lead wire insertion hole in the present invention does not have output abnormality in the oxygen concentration sensor even after three spray cycles, compared with the conventional oxygen concentration sensor not having a rib in the lead wire insertion hole which has an abnormal output after only one cycle, which indicates that the oxygen concentration sensor according to the present invention does not lose the function as an oxygen concentration sensor when sprayed with water.

Based on the above, is obvious that the oxygen concentration sensor according to the present invention has excellent water resistance.

Figure 11:
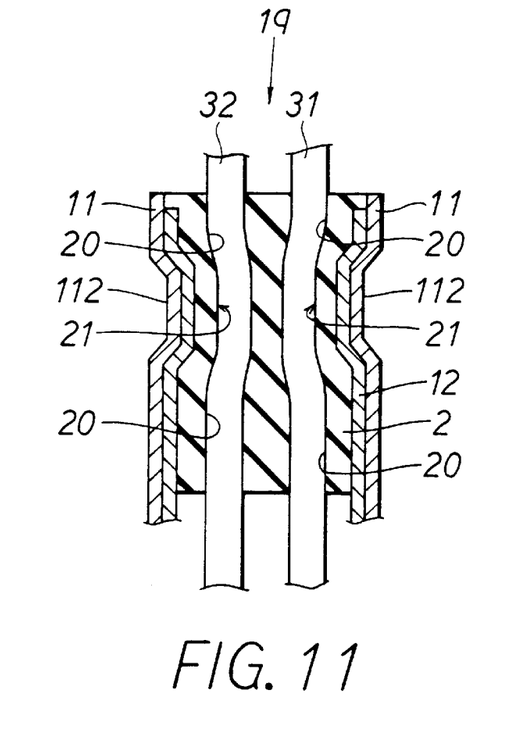
FIG. 11 is a longitudinal cross-sectional view of a main portion of an oxygen concentration sensor according to a second preferred embodiment according to the present invention.
Figure 12A:
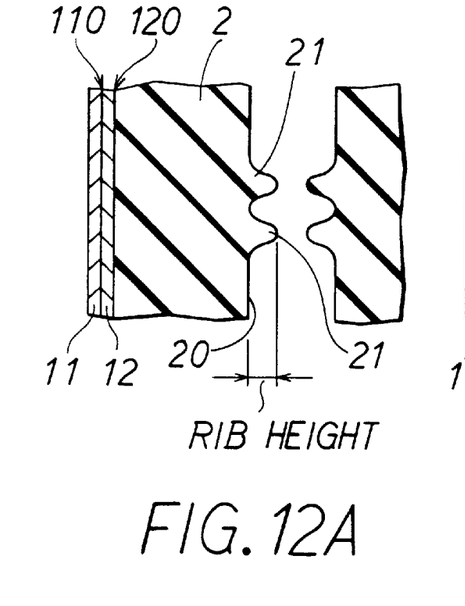
FIG. 12A is a longitudinal cross-sectional view of a sealing member according to the second embodiment before caulking a rib.
Figure 12B:
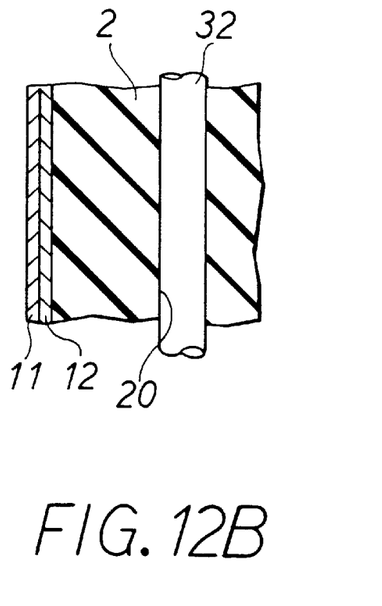
FIG. 12B is a longitudinal cross-sectional view thereof after caulking the rib.
Figures 13A, 13B:
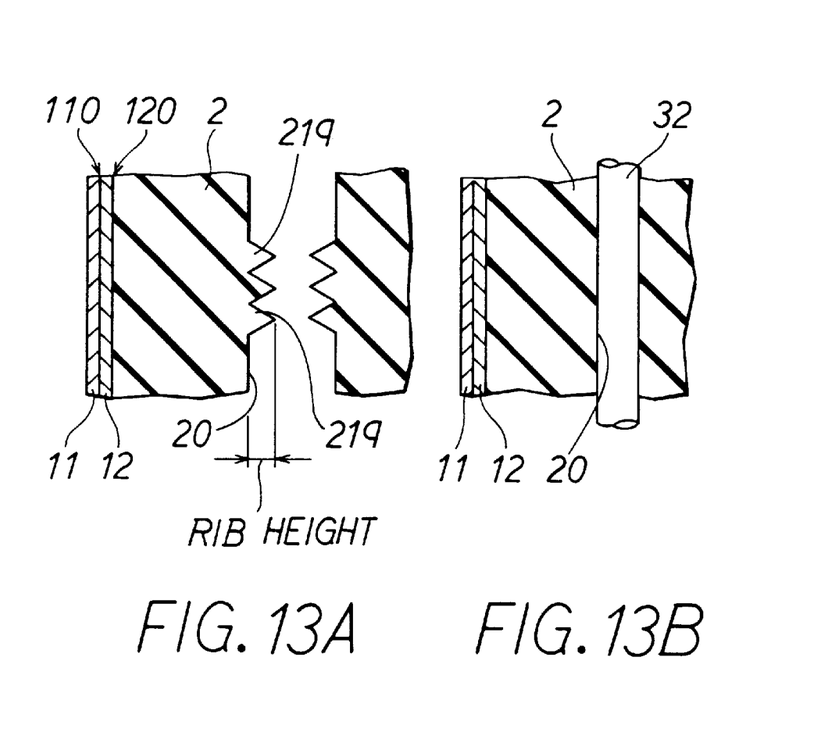
FIG. 13A is a longitudinal cross-sectional view of a sealing member according to a variation on the second embodiment before caulking a rib.
FIG. 13B is a longitudinal cross-sectional view thereof after caulking the rib.

A second preferred embodiment is hereinafter described with reference to the accompanying drawings. As shown in FIGS. 11–13, the rib 21 on the elastic insulating member 2 is caulked from the outside by the protective covers 11 and 12, which supports the lead wires 31 and 32 in an oxygen concentration sensor 19.

As shown in FIG. 12A, the rib 21 protrudes in an arc shape on the inner wall of the lead wire insertion hole 20 and is shaped like a continuous ring having two steps up and down in the axial direction of the elastic insulating member. Furthermore, as shown in FIG. 13A, the above-described shaped rib 21 can be replaced by a rib 219 protruding in the shape of three triangles on the inner wall of the lead wire insertion hole 20.

The portion having a rib 21 on the elastic insulating member 2 in an oxygen concentration sensor 19 is caulked by the protective covers 11 and 12 from the outside in the diametrical direction according to the present embodiment. Thus, the above rib 21 is in a completely crushed state as shown in FIGS. 12B and 13B to fill up the clearance between the lead wire insertion hole 20 and the lead wires 31 and 32 completely.

Accordingly, even if the ribs 2 and 219 do not deform in the operation of just press-fitting the lead wires 31 and 32 due to a difference between the diameters of the lead wires 31 and 32 and the diameter of the lead wire insertion hole 20, the lead wires 31 and 32 can stably and surely seal the lead wire insertion hole 20. Therefore, it is not necessary to worry about dimensional accuracy of the lead wires 31 and 32 and the lead wire insertion hole 20, thereby ensuring a certain allowance between the lead wires 31 and 32 and the lead wire insertion hole 20 in view of dimensional design. Thus, both can be easily installed in the present embodiment. Moreover, they can be manufactured at low cost.

Although the protective covers 11 and 12 are caulked until the rib 21 is completely crushed, it is also possible to permit a small clearance between the lead wires 31 and 32 and the lead wire insertion hole 20 with the rib 21 keeping its own shape to some extent as in the first embodiment.

A third preferred embodiment is hereinafter described with the accompanying drawings.

According to the present embodiment, as shown in FIGS. 14–18, an air inlet 299 passing through the inside of an oxygen concentration sensor 5 is disposed in an elastic insulating member 29. In addition, the oxygen concentration sensor 5 has a hard water repellent filter 59 disposed in the air inlet 299. The above water repellent filter 59 is molded from porous PTFE resin foam.

Figure 14:
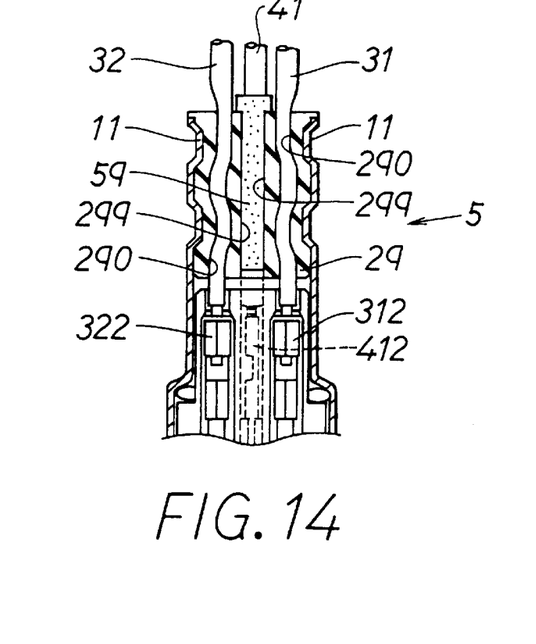
FIG. 14 is a cross-sectional view of a main portion of an oxygen concentration sensor having an elastic insulating member with an air inlet according to a third preferred embodiment of the present invention.
Figure 15:
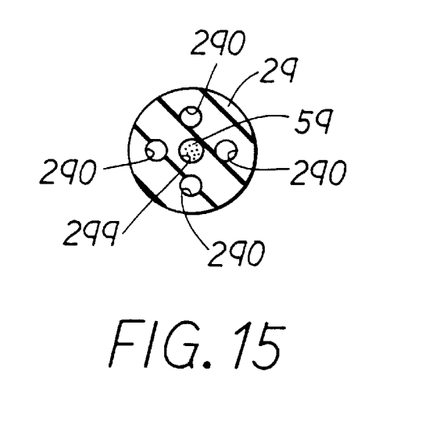
FIG. 15 is a radial cross-sectional view of the elastic insulating member according to the third embodiment.
Figure 16:
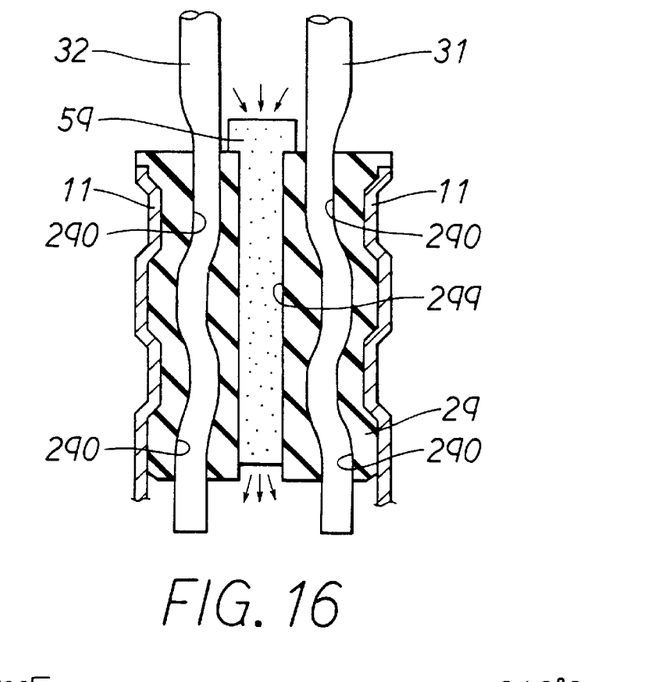
FIG. 16 is an enlarged cross-sectional view of a main portion of an oxygen concentration sensor according to the third embodiment.

As shown in FIGS. 14–16, the air inlet 299 is disposed at the center of the elastic insulating member 29, i.e., at the center of four lead wire insertion holes 290.

Figure 17A:
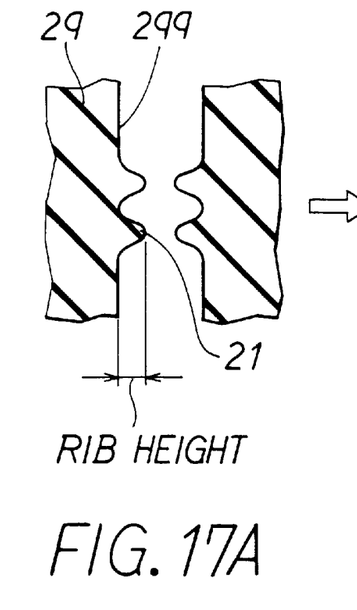
FIG. 17A is a longitudinal cross-sectional view of a sealing member according to the third embodiment before caulking a rib.
Figure 17B:
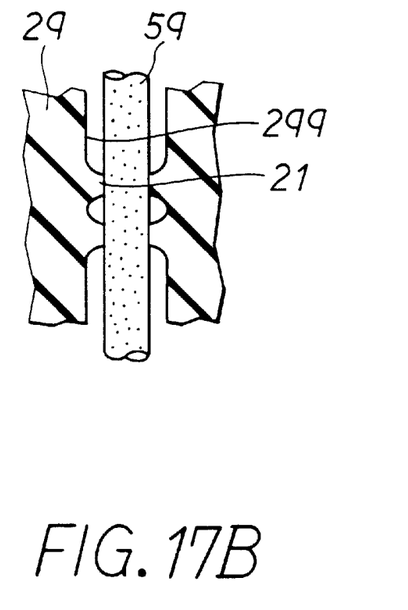
FIG. 17B is a longitudinal cross-sectional view thereof after caulking the rib.

As shown in FIG. 17A, the rib 21 is also disposed in the air inlet 299. The rib 21 has a similar shape to the one provided for the lead wire insertion hole 290, and it protrudes in an arc shape on the inner wall of the air inlet 299 and is formed in the shape of a continuous two-step ring in the central axial direction of the elastic insulating member. The portion having the rib 21 on the elastic insulating member 29 is caulked by the above-described protective covers 11 and 12 to hold the lead wires 31, 32, and 41 and the water repellent filter 59. Since the rib 21 is caulked in the above-described manner, it is in a state of deformation as shown in FIG. 17B.

Figure 18A:
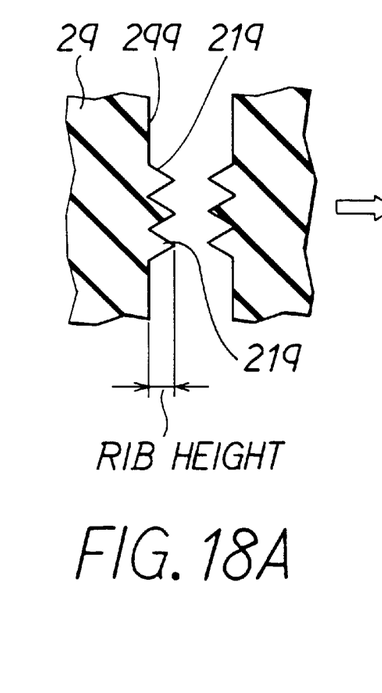
FIG. 18A is a longitudinal cross-sectional view of a sealing member according to a variation on the third embodiment before caulking a rib.
Figure 18B:
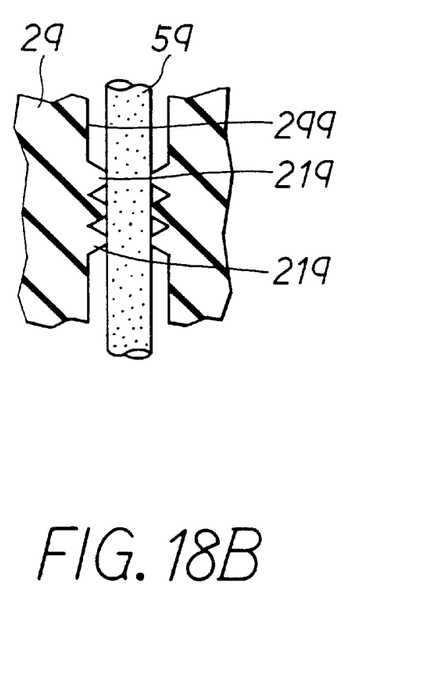
FIG. 18B is a longitudinal cross-sectional view thereof after caulking the rib.

Furthermore, as shown in FIG. 18A, the rib 219 can be disposed in the shape of three triangles on the inner wall of the air inlet 299. The rib 219 deforms as shown in FIG. 18B when it is caulked by the protective covers 11 and 12 as described above.

The water repellent filter 59 is disposed at the center of the four lead wire insertion holes 290, i.e., at the portion to make the thickness difference of the elastic insulating member 29 smaller, so that the stress imposed on each portion of the elastic insulating member 29 can be more even.

In a conventional oxygen concentration sensor, air has been introduced through a small hole disposed at the side surface of the protective cover or the like, or in case the protective cover is composed of plural covers, it has been done through a clearance between adjacent covers. On the other hand, in the oxygen concentration sensor 5 according to the present embodiment, the open end of the air inlet 299 is disposed at the upper portion of the elastic insulating member 29, so that the air can be introduced and expelled as shown with arrows in FIG. 16.

In accordance with the present embodiment, easy assembling and installation of components can be ensured and a sufficient amount of the air can be introduced inside the oxygen concentration sensor 5. Therefore, even if air/fuel ratio tends to the rich side and a large amount of reference gas is required, the air/fuel ratio can be detected with high accuracy.

Figure 19:
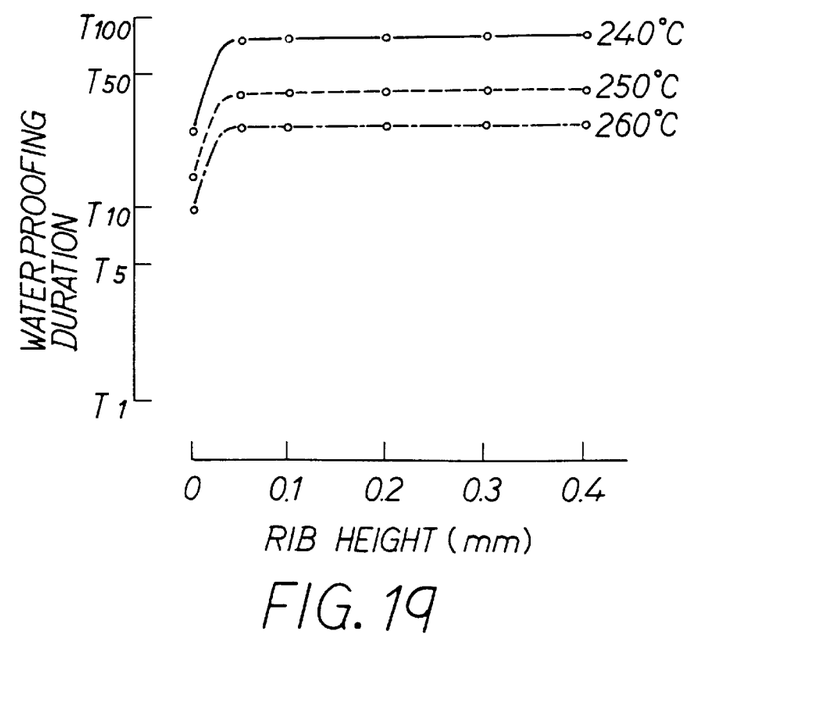
FIG. 19 is a graph showing the relation between water resistance life and the height of a rib.

FIG. 19 explains the relation between the height of the rib disposed in the lead wire insertion portion and water resistant life in the oxygen concentration sensor. The water resistant life of the present embodiment has been measured based on the oxygen concentration sensor shown in FIG. 5 having the elastic insulating member shown in FIG. 2B of the first embodiment.

However, a total of five different standard oxygen concentration sensors, ranging from one which does not have a rib, i.e., the height of the rib is zero, to ones having a rib whose height is up to 0.4 mm, have been prepared. The same method as in the third embodiment is used for this measurement. The temperature of the elastic insulating members in the oxygen concentration sensors are adjusted to be 240° C., 250° C., and 260° C. in the measurement, of which results are shown in FIG. 19.

According to the graph, the water resistance lifetime is remarkably extended when the height of the rib is 0.05 mm or more. Furthermore, such an improved life of the water resistance can be confirmed in respective cases of 240° C., 250° C., and 260° C.

Judging from the above results, an oxygen concentration sensor having a long life of excellent water resistance can be obtained by disposing the rib related to the present invention in the lead wire insertion hole.

Although the present invention has been fully described in connection with the preferred embodiment thereof with reference to the accompanying drawings, it is to be noted that various changes and modifications will become apparent to those skilled in the art. Such changes and modifications are to be understood as being included within the scope of the present invention as defined by the appended claims.

What is claimed is:

1. An electrical device comprising:

an electrical element disposed in a housing;

a protective cover enclosing at least a portion of said housing;

a lead wire passing through said protective cover;

an elastic insulating member disposed inside said protective cover and having a lead wire insertion hole receiving said lead wire; and a lead wire insertion hole rib protruding from said elastic insulating member in a radial direction of said lead wire insertion hole; wherein said elastic insulating member is fixed by said protective cover to have a predetermined position.

2. An electrical device according to claim 1, wherein said lead wire insertion hole rib on said elastic insulating member is fixed to have a predetermined position by said protective cover.

3. An electrical device comprising:

an electrical element disposed in a housing;

a protective cover enclosing at least a portion of said housing;

a lead wire passing through said protective cover;

an elastic insulating member disposed inside said protective cover and having a lead wire insertion hole receiving said lead wire;

a lead wire insertion hole rib protruding from said elastic insulating member in a radial direction of said lead wire insertion hole;

an air introducing inlet, penetrating said electrical device through said elastic insulating member and said protective cover; and a hard water repellent filter disposed in said air introducing inlet;

wherein said elastic insulating member is fixed by said protective cover to have a predetermined position; and said lead wire insertion hole rib on said elastic insulating member is fixed to have a predetermined position by said protective cover.

4. An electrical device according to claim 3, wherein said air introducing inlet is disposed at a radially central position of said elastic insulating member.

5. An electrical device according to claim 4, further comprising a rib portion protruding in a radial direction of said air introducing inlet.

6. An electrical device according to claim 5, wherein said rib portion is in a shape of a continuous ring.

7. An electrical device according to claim 6, wherein a height of said rib portion is 0.05–0.4 mm in a free state before being crimped.

8. An electrical device according to claim 3, further comprising a rib portion protruding in a radial direction of said air introducing inlet.

9. An electrical device according to claim 8, wherein said rib portion is in a shape of a continuous ring.

10. An electrical device according to claim 9, wherein a height of said rib portion is 0.05–0.4 mm in a free state before being crimped.

11. An electrical device comprising:

an electrical element disposed in a housing;

a protective cover enclosing at least a portion of said housing;

a lead wire passing through said protective cover;

an elastic insulating member disposed inside said protective cover and having a lead wire insertion hole receiving said lead wire;

a lead wire insertion hole rib protruding from said elastic insulating member in a radial direction of said lead wire insertion hole;

an air introducing inlet penetrating inside said electrical device through said elastic insulating member and said protective cover; and a hard water repellent filter disposed in said air introducing inlet;

wherein said elastic insulating member is fixed by said protective cover to have a predetermined position.

12. An electrical device according to claim 11, further comprising a rib portion protruding in a radial direction of said air introducing inlet.

13. An electrical device according to claim 12, wherein said rib portion is in a shape of a continuous ring.

14. An electrical device according to claim 13, wherein a height of said rib portion is 0.05–0.4 mm in a free state before being crimped.

15. An electrical device according to claim 11, wherein said air introducing inlet is disposed at a center of said elastic insulating member.

16. An electrical device according to claim 15, further comprising an rib portion protruding in a radial direction of said air introducing inlet.

17. An electrical device according to claim 16, wherein said rib portion is in a shape of a continuous ring.

18. An electrical device according to claim 17, wherein a height of said rib portion is 0.05–0.4 mm in a free state before being crimped.

19. An electrical device according to claim 1, wherein said lead wire insertion hole rib is in a shape of a continuous ring.

20. An electrical device comprising:

an electrical element disposed in a housing;

a protective cover enclosing at least a portion of said housing;

a lead wire passing through said protective cover;

an elastic insulating member disposed inside said protective cover and having a lead wire insertion hole receiving said lead wire;

a lead wire insertion hole rib protruding from said elastic insulating member in a radial direction of said lead wire insertion hole;

wherein said elastic insulating member is fixed by said protective cover to have a predetermined position;

said lead wire insertion hole rib is in a shape of a continuous ring; and a height of said lead wire insertion hole rib is 0.05–0.4 mm in a free state before being crimped.

21. An electrical device comprising:

an electrical element disposed in a housing;

a protective cover enclosing at least a portion of said housing;

a lead wire passing through said protective cover;

an elastic insulating member fixed by said protective cover to have a predetermined position, disposed in side said protective cover and having a lead wire insertion hole receiving said lead wire; and a rib contacting said lead wire and said elastic insulating member and forming a seal therebetween.

22. An electrical device of claim 21, wherein said rib is integral with said elastic insulating member.

23. An electrical device according to claim 1, wherein said lead wire insertion hole rib protrudes from said elastic insulating member in said lead wire insertion hole.

24. An electrical device of claim 21, wherein said rib contacting said lead wire, and said elastic insulating member, is in said lead wire insertion hole.

25. An electrical device comprising:

a housing;

an electrical element disposed in said housing;

a protective cover enclosing at least a portion of said housing;

an elastic insulating member disposed in said protective cover and having a lead wire insertion hole with a rib, said rib protruding from an inner surface of said lead wire insertion hole; and a lead wire inserted into said lead wire insertion hole and deforming said rib in said lead wire insertion hole.

* * * * *